US011961613B2

(12) United States Patent
Bolneni et al.

(10) Patent No.: US 11,961,613 B2
(45) Date of Patent: Apr. 16, 2024

(54) INVENTORY SYSTEM, DEVICES, AND METHODS THEREOF

(71) Applicant: MedVision AI Corp., Ypsilanti, MI (US)

(72) Inventors: Anurag Bolneni, Troy, MI (US); Raghu Arghal, Philadelphia, PA (US); Nathan Block, Dallas, TX (US)

(73) Assignee: MedVision AI Corp., Ypslilanti, MI (US)

(*) Notice: Subject to any disclaimer, the term of this patent is extended or adjusted under 35 U.S.C. 154(b) by 0 days.

(21) Appl. No.: 17/822,312

(22) Filed: Aug. 25, 2022

(65) Prior Publication Data

US 2023/0260631 A1    Aug. 17, 2023

Related U.S. Application Data

(60) Provisional application No. 63/309,472, filed on Feb. 11, 2022.

(51) Int. Cl.
| | | |
|---|---|---|
| *G06F 13/38* | (2006.01) | |
| *G01G 19/52* | (2006.01) | |
| *G06Q 10/00* | (2023.01) | |
| *G06Q 10/08* | (2023.01) | |
| *G06Q 10/087* | (2023.01) | |

(Continued)

(52) U.S. Cl.
CPC .............. *G16H 40/20* (2018.01); *G01G 19/52* (2013.01); *G06Q 10/087* (2013.01)

(58) Field of Classification Search
CPC ....... G16H 40/20; G01G 19/52; G06Q 10/087
See application file for complete search history.

(56) References Cited

U.S. PATENT DOCUMENTS

| | | |
|---|---|---|
| 7,844,509 B2 | 11/2010 | Bodin et al. |
| 10,121,121 B1 | 11/2018 | De Bonet et al. |
| 10,318,917 B1 | 6/2019 | Goldstein et al. |

(Continued)

OTHER PUBLICATIONS

Fast Solutions, "View Real-Time Inventory Data, Anytime, Anywhere," Published in U.S.A, 2 pp., https://www.fastenal.com/content/documents/web/solutions/FAST_Scale_Brochure.pdf, last accessed Nov. 11, 2022; also available at https://web.archive.org/web/20151017164445/https://www.fastenal.com/content/documents/web/solutions/FAST_Scale_Brochure.pdf, dated Oct. 17, 2015.

*Primary Examiner* — Maroun P Kanaan
(74) *Attorney, Agent, or Firm* — Bodman PLC

(57) ABSTRACT

An inventory system includes one or more shelving units and an inventory computing system. The shelving units each include shelves for storing medical supplies, a control system, and a communications interface. The shelves include shelf locations that each include one or more weight sensors for measuring weight thereon. The control system is in communication with the weight sensors for receiving measurement signals therefrom and causing the communications interface to send weight measurements for each of the shelf locations of each of the shelves determined according to the measurement signals. The inventory computing system is in communication with each of the shelving units via a network to receive the weight measurements for the shelf locations. The inventory computing system determines quantities of the medical supplies stored on each of the shelf locations according to the one or more weight measurements.

20 Claims, 8 Drawing Sheets

(51) Int. Cl.
*G06Q 30/00* (2023.01)
*G16H 40/20* (2018.01)

(56) References Cited

U.S. PATENT DOCUMENTS

| | | |
|---|---|---|
| 10,332,066 B1 | 6/2019 | Palaniappan et al. |
| 11,030,571 B2 | 6/2021 | Glasgow et al. |
| 2003/0126613 A1* | 7/2003 | McGuire ............ H04N 21/4622 715/745 |
| 2008/0183599 A1 | 7/2008 | Hill et al. |
| 2018/0114184 A1* | 4/2018 | Brooks .................. G01G 23/18 |
| 2021/0133835 A1* | 5/2021 | Gu ......................... G06Q 10/08 |
| 2022/0104636 A1* | 4/2022 | Chila ...................... G16H 40/20 |
| 2022/0335726 A1* | 10/2022 | Paverman Kashani ... G06T 7/73 |

\* cited by examiner

INVENTORY SYSTEM, DEVICES, AND METHODS THEREOF

CROSS-REFERENCE TO RELATED APPLICATION(S)

This application claims priority to and the benefit of U.S. Provisional Patent Application No. 63/309,472, filed Feb. 11, 2022, the entire disclosure of which is incorporated by reference herein.

TECHNICAL FIELD

This disclosure relates to inventory systems and, in particular, inventory systems for medical settings.

BACKGROUND

Inventory systems typically require inventorying individual units of products, which can be time consuming and disrupt workflows in fast-paced environments, such as in a medical environment (e.g., a hospital). An inventorying system, such as a medical supply inventorying system, or inventorying system for other goods or supplies, that tracks quantities of goods and supplies, such as medical supplies or other types of goods and supplies, but does not require tracking usage of individual units of products would be advantageous.

SUMMARY

Disclosed herein are implementations of inventory systems. In an implementation, an inventory system includes a shelving unit and an inventory computing system. The shelving unit includes one or more shelves, a control system, and a communications interface. Each of the shelves includes shelf locations that each include one or more weight sensors for measuring weight thereupon. The control system is in communication with the weight sensors for receiving measurement signals therefrom and sends, via the communications interface, weight measurements for each of the shelf locations of each of the shelves. The inventory computing system is in communication with the shelving unit via a network to receive the weight measurements for each of the shelf locations. The inventory computing system determines a quantity of medical supplies associated with each shelf location according to the weight measurements.

In an implementation, an inventory system includes one or more shelving units and an inventory computing system. The shelving units each include shelves for storing medical supplies, a control system, and a communications interface. The shelves include shelf locations that each include one or more weight sensors for measuring weight thereon. The control system is in communication with the weight sensors for receiving measurement signals therefrom and causing the communications interface to send weight measurements for each of the shelf locations of each of the shelves determined according to the measurement signals. The inventory computing system is in communication with each of the shelving units via a network to receive the weight measurements for the shelf locations. The inventory computing system determines quantities of the medical supplies stored on each of the shelf locations according to the one or more weight measurements.

The inventory system may be configurable to associate, with the inventory computing system, any one of the shelf locations with a first of the medical supplies and any two adjacent ones of the shelf locations with a second of the medical supplies. The inventory computing system may determine a first quantity of the first medical supply according to the weight measurements for the one shelf location, and may determine a second quantity of the second medical supply according to the weight measurements for the two adjacent shelf locations. Each of the shelving unites may include a shelving structure that is cooperatively configured with the shelves for the shelves to be moved between different vertical shelf positions and to electrically couple the weight sensors of the shelves to a controller of the control system at each of the vertical shelf positions. Each of the shelving units may be configured to communicate with the inventory computing system predominantly cellularly independent of the other network and secondarily with the other network.

In an implementation, a shelving system includes a shelving unit and a control system. The shelving unit includes shelves, weight sensors, and one or more activity sensors. The shelves include shelf locations thereon, which are discrete from each other. The weight sensors are each associated with one of the shelf locations for measuring weight of supplies positioned on the shelf location associated therewith. The one or more activity sensors are configured to detect physical activity associated with the shelf locations. The control system receives signals from the weight sensors and the one or more activity sensors and outputs to an inventory computing system weight measurements according to the weight sensors and activity information according to the one or more activity sensors.

In an implementation, a method for determining quantities of medical supplies includes: providing a shelving having one or more shelves storing medical supplies, each of the one or more shelves including shelf locations that each include one or more weight sensors for measuring weight of one of the medical supplies stored thereon; storing, with a computing system, for each medical supply, a supply identifier and an incremental weight; storing, with the computing system, for each shelf location, the supply identifier of the medical supply stored therein and one or both of the weight measured by the one or more weight sensors or a quantity of the medical supply stored thereon; measuring, with one or more weight sensors, the weights of the medical supplies stored on the shelf locations; and determining, with the computing system, the quantity of each of the medical supplies at each of the shelf locations according to the incremental weight of the medical supply and the weight measured at the shelf location.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
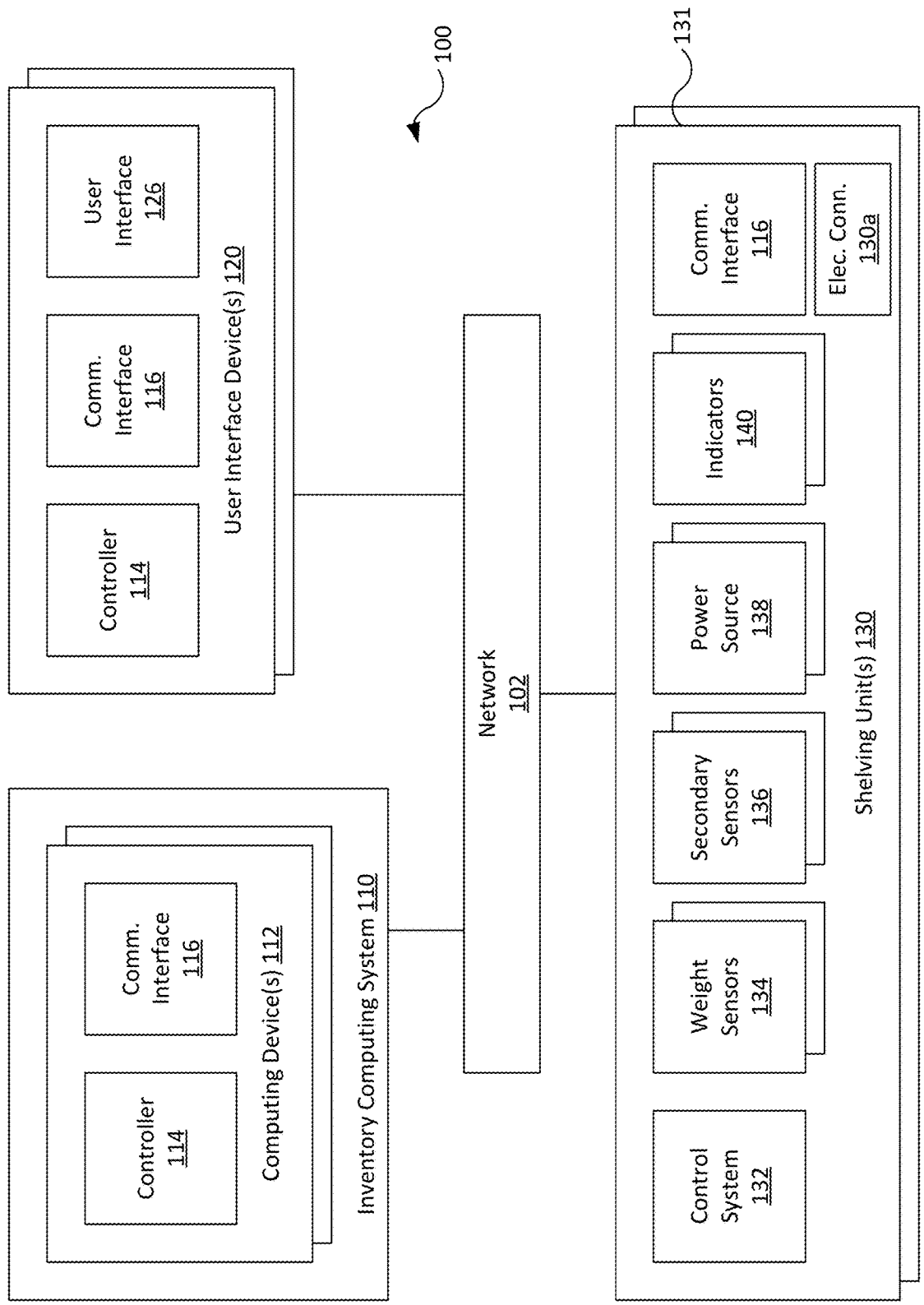
FIG. 1 is a schematic view of an inventory system.

Referring to FIG. 1, an inventory system 100 is configured to monitor inventories of medical supplies stored within and across medical care systems, campuses, buildings, and/or storage areas thereof. The inventory system 100 may instead be configured to monitor inventories of other goods and supplies stored within and across different businesses, campuses, buildings, and storage areas thereof. The inventory system 100 uses weight-based measurements to estimate (e.g., determine) quantities of medical supplies. While not as precise and having other possible error sources as compared to traditional inventorying systems (e.g., individually inventorying or otherwise individually tracking units or packages of medical supplies), the inventory system 100 removes and/or does not impose on users of the medical supplies those barriers or other friction of such traditional inventorying systems, while still allowing medical supply managers to monitor medical supply inventories more efficiently and more precision than human-based inventorying.

The inventory system 100 generally includes an inventory computing system 110, one or more user interface devices 120, and one or more shelving units 130 in communication therewith via a network 102.

The network 102 may include any suitable hardware and configurations suitable for the inventory computing system 110, the user interface devices 120, and the shelving units 130 to be in communication with each other. In some instances, the network 102 may be a local network of the medical building or campus in which the inventory system 100 is incorporated or may further include or otherwise interface with cellular networks. Cellular networks may, for example, be a primary or backup system for communicating between the inventory computing system 110, the user interface devices 120, and/or the shelving units 130 when other network hardware is unavailable (e.g., if a local network of the building or campus is out of service). In one preferred embodiment, the shelving units 130 are configured to communicate with the network 102 and, ultimately, the inventory computing system 110 cellularly independent of a network of a facility (e.g., Wi-Fi or LAN) in which the shelving units 130 are located. For example, the shelving units 130 may be configured to communicate with the network 102 and the inventory computing system 110 only cellularly and independent of the other network of the facility. Alternatively, the shelving units 130 may be configured (e.g., with software instructions) to communicate with the network 102 and the inventory computing system 110 predominantly cellularly (e.g., 90% or more of the time and/or unless a fault in cellular communication occurs) and secondarily via the other network of the facility (e.g., 10% or less of the time and/or when a fault in cellular communication occurs). In another example, the shelving units 130 may be configured to communicate with the network 102 and the inventory computing system 110 predominantly via the other network of the facility and secondarily cellularly (e.g., in case of fault of the other network).

It should be noted that the shelving units 130 may communicate with each other via any suitable means (e.g., via any suitable wired or wireless manner) and may thereby communicate indirectly with the network 102 and, ultimately, to the inventory computing system 110. Furthermore, while the shelving units 130 may communicate with each other and form a network in and of themselves, the shelving units 130 are not considered part of the network 102 (e.g., of the facility in which they are located) but rather communicate with the network 102. In some instances, some of the shelving units 130 may be configured to communicate with other shelving units 130 but not directly with the network 102 (e.g., via hardware and/or software configurations), while one or more others of the shelving units 130 are configured to communicate with both others of the shelving units 130 and the network 102, including sending information from the other shelving units 130 to the inventory computing system 110.

The inventory computing system 110 is generally configured to determine current inventories of medical supplies stored by the one or more shelving units 130, and may also provide various additional functionality, such as locating medical supplies, tracking historical usage of supplies, automated ordering of medical supplies, and identifying aberrant usage trends or inventories of medical supplies.

The inventory computing system 110 includes one or more computing devices 112, each of which may generally include a controller 114 and a communications interface 116. The controller 114 may have a hardware configuration as described with respect to FIG. 2. The communications interface 116 is configured for the inventory computing system 110 to communicate with other aspects of the inventory system 100, for example, including suitable devices (e.g., modems) for communication via the network 102. The inventory computing system 110 may, for example, be a server computer that is located remotely from the building or campus in which the shelving units 130 are located.

Further aspects of the inventory computing system 110 are discussed in further detail below.

Figure 2:
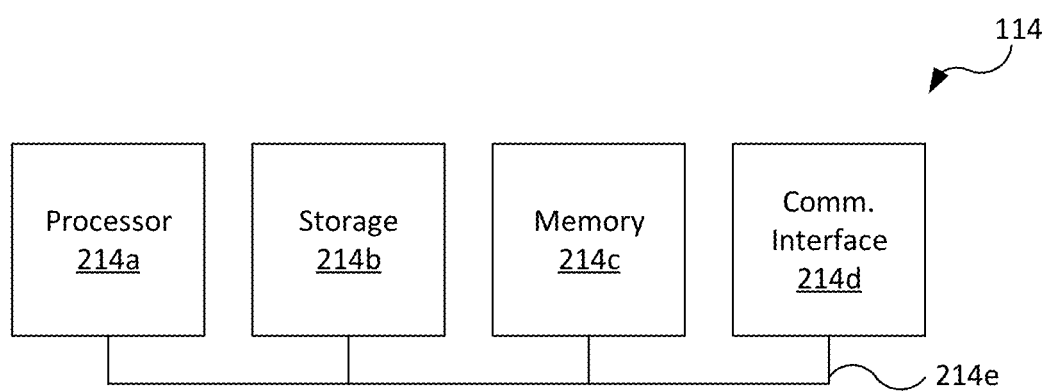
FIG. 2 is a schematic view of an example hardware configuration for a controller of a computing device of the inventory system.

Referring to FIG. 2, an example hardware configuration is illustrated for the controller 114. The controller 114 generally includes a processor 214a, a storage 214b, a memory 214c, and a communications interface 214d that are in communication with each other (e.g., via a bus 214e). The processor 214a may be any processing device capable of executing instructions (e.g., software) in the storage 214b, such as a central processing unit (CPU). The storage 214b is a non-volatile, long-term storage device, such as a solid state or hard disc drive. The storage 214b may be considered to form a machine- or computer-readable medium. The memory 214c is a volatile, short-term storage device, such as a random access memory (RAM) module. The communications interface 214d is configured to send to and receive signals from other aspects of the inventory computing system 110, such as the communications interface 116.

Referring again to FIG. 1, each of the user interface devices 120 is a computing device (e.g., smartphone, tablet computer) configured for users to configure the inventory system 100 and the shelving units 130 thereof, manually adjust inventories, troubleshoot inventory errors, and/or see current inventories. The user interface device 120 generally includes a controller 114, a communications interface 116, and a user interface 126. The controller 114 of the user interface device 120 is configured to operate the other components of the user interface device 120 (e.g., the communications interface 116 and/or the user interface 126) according to the methods and instructions described herein.

The communications interface 116 of the user interface device 120 is configured to send and/or receive signals to and from other aspects of the inventory system 100, including the inventory computing system 110 and/or the shelving units 130 using any suitable protocols and/or devices (e.g., via the network 102 via wired connections, Wi-Fi, Bluetooth, and/or cellular devices). The user interface 126 generally includes input devices that receive inputs from the user and output devices that provide outputs (e.g., graphics) to the user, such as a touch screen display, buttons, cameras, microphones, and/or speakers.

Still referring to FIG. 1, the shelving units 130 are configured hold the medical supplies thereon, and measure and send weight measurements according to which inventories of the medical supplies can be calculated by the inventory computing system 110. Each of the shelving units 130 generally includes a shelving structure 131, a control system 132, weight sensors 134, secondary sensors 136, a power source 138, and the communications interface 116. The shelving units 130 may further include indicators 140.

The shelving structure 131 is configured to support the medical supplies thereon. Various different shelving structures 131 are discussed in further detail below. The weight sensors 134 are configured to measure weights of the medical supplies on the shelving structure 131. The secondary sensors 136 are configured to monitor other conditions pertaining to the shelving units 130. For example, the secondary sensors 136 may be configured to detect motion (e.g. indicative of a user removing medical supplies from the shelving unit 130) and/or detecting radio-frequency identification (RFID) tags (e.g., on containers associated with particular medical supplies). The power source 138 is configured to supply power to the other electronic components of the shelving unit 130, may be configured to store energy (e.g., include a battery), and/or supply power to other shelving units 130 (e.g., being interconnected therewith). For example, each of the shelving units 130 may include electrical connectors 130a (e.g., plugs and receptacles; depicted schematically in FIG. 1) to connect to each other serially and/or in parallel to transfer power and/or data therebetween.

The control system 132 is configured to operate the other components of the shelving units 130 according to the methods and instructions described herein. The control system 132 is discussed in further detail below with respect to FIG. 6 and may include a controller (e.g., a primary controller) that may be configured as described for the controller 114.

The communications interface 116 is configured to send and/or receive signals to and from other aspects of the inventory system 100, including the inventory computing system 110, the user interface devices 120, and/or others of the shelving units 130 directly or indirectly (e.g., via the network 102). The shelving units 130 may, for example, be configured to communicate directly with each other (e.g., via wired connection), while only one of the shelving units 130 may include the communications interface 116 configured to communicate via cellular networks.

Figure 3:
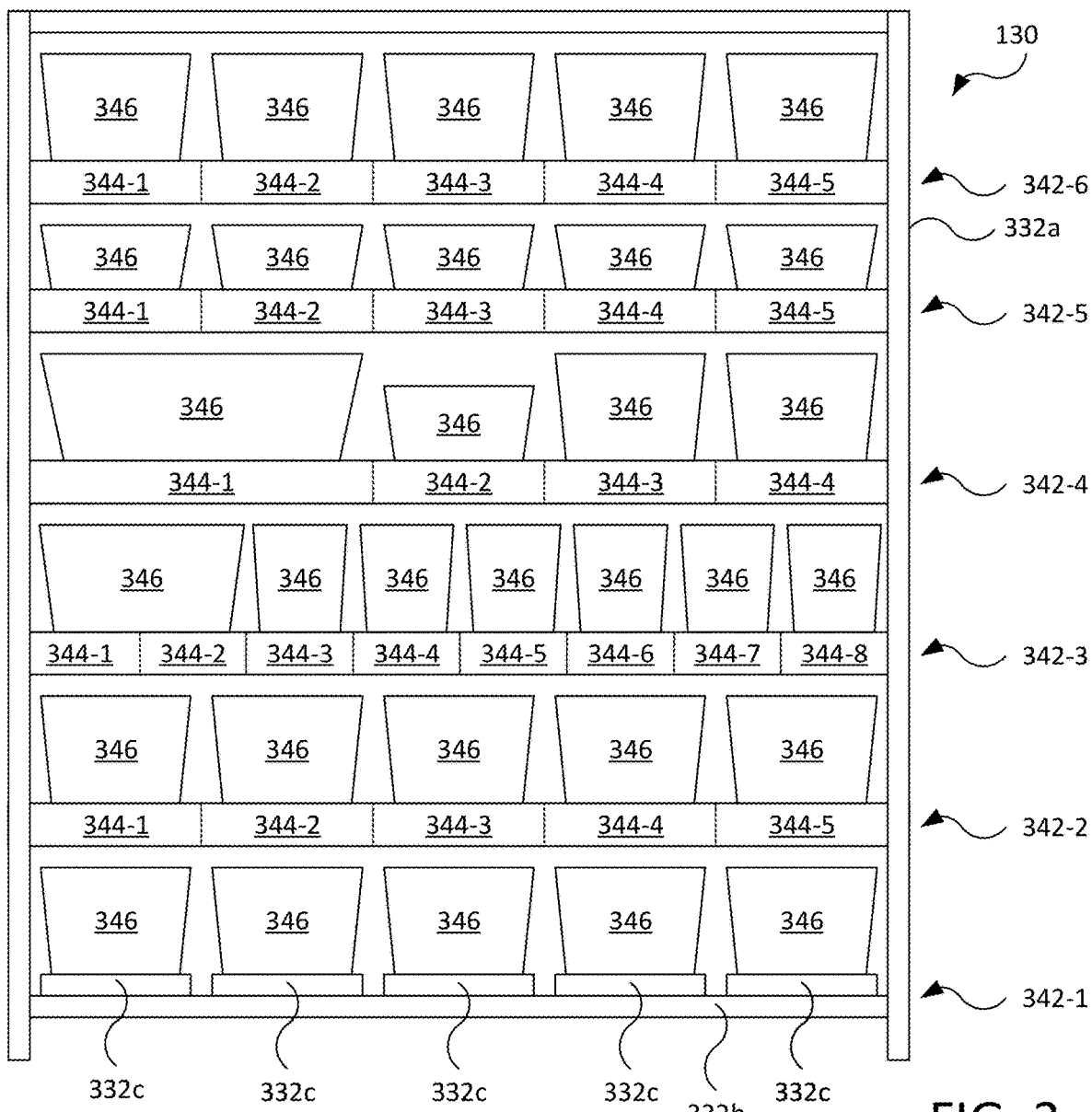
FIG. 3 is a front view of a shelving unit of the inventory system.
Figure 4:
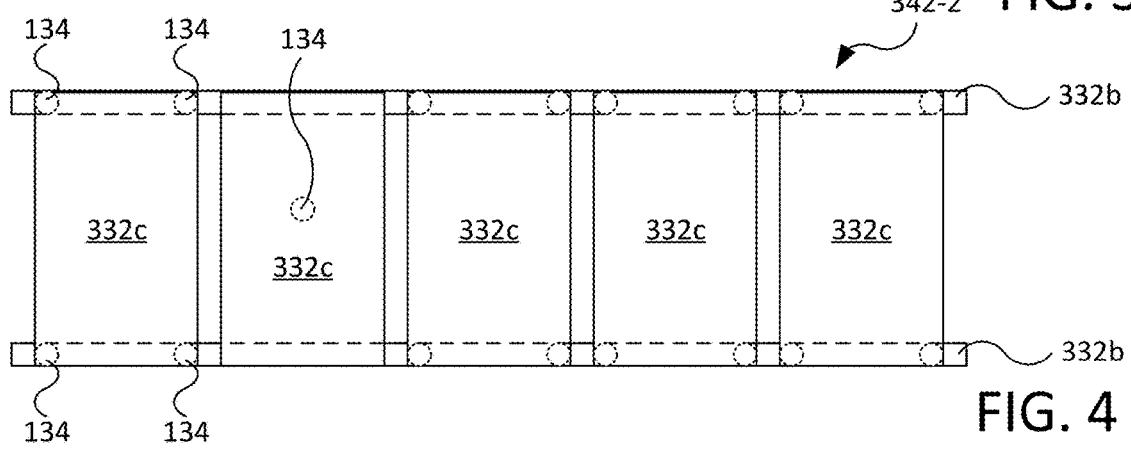
FIG. 4 is a top view of a shelf of the shelving unit.

Referring to FIGS. 3-4, the shelving unit 130 includes shelves 342 that define shelf locations 344 thereon. For example, the shelving unit 130 may include M of the shelves 342-1 to 342-M, where M is the number of the shelves 342 and may be between four and ten, more or less. Each shelf 342 may include N of the shelf locations 344 spread laterally (i.e., left-to-right) thereacross, where N is the number of storage locations and may be between four and twenty, more or less. The shelves 342 are configured to support containers 346 of the medical supplies at each of the shelf locations 344. The shelf locations 344 are discrete locations at which the shelving unit 130 measures the weight supported by the shelf 342 at that shelf location 344 independent of all others of the shelf locations 344 on that same shelf 342, such as the container 346 of medical supplies thereon.

The shelves 342 and the shelf locations 344 may be configured in different manners. In one example, the shelves 342 may be spaced apart at uniform heights, each shelf 342 includes the same number of shelf locations 344, and the shelf locations 344 have the same width. Such a uniform configuration within the shelving unit 130 and between the shelving units 130 may allow for simplified manufacturing and/or configuring of the shelving unit 130 for inventorying (e.g., associating different medical supplies with different ones of the shelf locations 344).

Alternatively, the shelves 342 may be spaced apart different vertical distances (e.g., the shelf 342-5 compared to the other shelves 342), the shelves 342 may have different numbers of shelf locations 344 (e.g., the shelf 342-3 and 342-4 compared to the other shelves 342), and/or have shelf locations 344 of varying widths (e.g., the shelf 342-4). Furthermore, while each one the shelf locations 344 is intended to be associated with only one of the containers 346, one of the containers 346 (and, thereby, the medical supply stored therein) may be associated with multiple adjacent ones of the shelf locations 344 (e.g., on the shelf 342-3, the left-most container 346 is associated with both of the shelf locations 344-1, 344-2 that are adjacent to each other). Association of the containers 346 and/or the medical supplies thereof with the shelf locations 344 is discussed in further detail below with respect to the inventory computing system 110 and the user interface device 120.

As referenced above, each of the shelving units 130 includes a shelving structure 131 that supports and/or forms the shelves 342. The shelving structure 131 generally includes vertical members 332a and, as illustrated for the shelf 342-1, horizontal members 332b. The vertical members 332a (e.g., legs, such as front and rear legs on left and right sides) support the horizontal members 332b (e.g., arms or shelf supports) extending left-to-right and/or front-to-back between the vertical members 332a) at spaced-apart vertical positions that may be adjustable or predefined. The horizontal members 332b may be coupled to the vertical members 332a in any suitable manner, for example, using threaded fasteners or protrusions (e.g., on the shelves 342, or vice versa) that are received in slots or apertures (e.g., on the vertical members 332a, or vice versa).

Figure 3A:
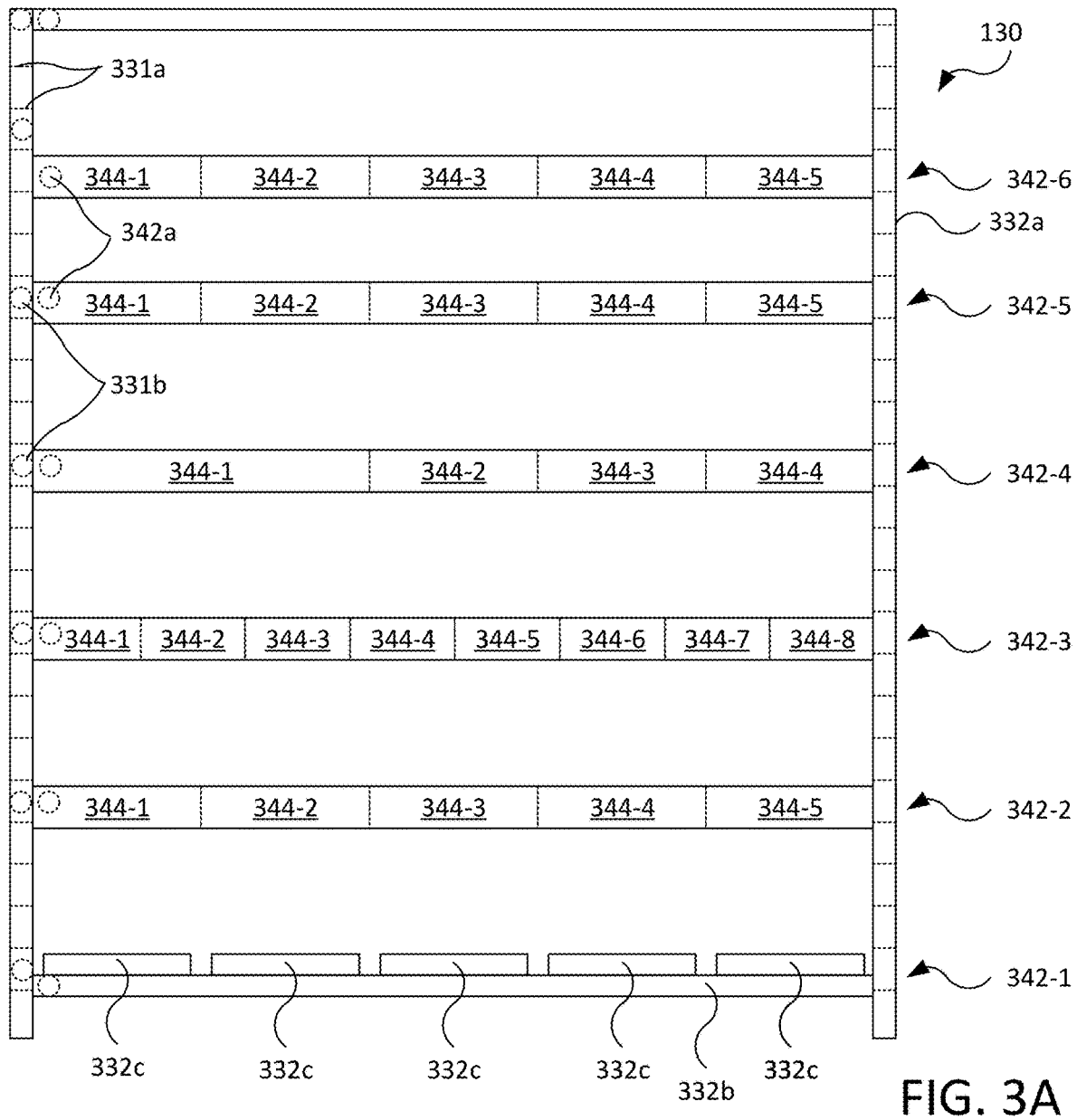
FIG. 3A is a front view of the shelving unit depicting shelf positions and electrical connectors.

Still referring to FIG. 3, each of the shelves 342 is supported by the horizontal members 332b at one of the spaced-apart vertical positions and may be considered to include the horizontal members 332b. Furthermore, the shelving structure 131 and the shelves 342 may be cooperatively configured for the shelves to be moved between the different vertical shelf positions 331a and to electrically couple electronic components for power and/or data transfer therebetween at each of the different vertical shelf positions 331a. For example, when positioned at any of the vertical shelf positions 331a, the weight sensors 134 of the shelves 342, as well as other electronic components of or coupled to the shelves, are electrically coupled to a controller (e.g., a primary controller 632c, discussed below) of the control system 132, as well as other electronic components of or coupled to the shelving structure 131, for power and/or data transfer therebetween. The shelving unit 130 is thereby configurable (e.g., modular) such that individual ones of the shelves 342 may be removed or moved to different locations within the shelving unit 130 (e.g., to accommodate taller and/or larger supplies thereon) or between shelving units 130. For example, referring to FIG. 3A, the shelving structure 131 may include vertical shelf positions 331a along the vertical members 332a that are discrete from each other and at which the shelving structure 131 supports the shelves 342. The vertical shelf positions 331a are depicted schematically with dotted lines in FIG. 3A. The vertical shelf positions 331a may be greater in number than the shelves 342 themselves, such that the shelves 342 may be adjustable in height. The vertical shelf positions 331a may, for example, be spaced apart approximately 6 inches, more or less. Alternatively, the shelves 342 may be infinitely adjustable in height along the vertical members 332a (e.g., using clamps or wedges to couple the shelves 342 to the vertical members 332a).

As referenced above, the shelving unit 130 is further configured to electrically couple the shelves 342 and the electronic components thereof (e.g., aspects of the control system 132, the weight sensors 134, the secondary sensors 136, and the indicators 140 coupled thereto) to other electronic components coupled of the shelving unit 130 (e.g., other aspects of the control system 132, the power source 138, and the communications interface 116 coupled to the shelving structure) to transfer data and power therebetween. To provide modularity of the shelving unit 130, the shelving structure 131 may include electrical connectors 331b that releasably connect with and, thereby, electrically couple to corresponding electrical connectors 342a of the shelves 342. The electrical connectors 331b, 342a are depicted schematically as dotted circles in FIG. 3A and schematically as female/male connectors in FIG. 6. The electrical connectors 331b, 342a may also be referred to as first electrical connectors and second electrical connectors to distinguish therebetween. The electrical connectors 331b of the shelving structure 131 may, for example, be receptacles that receive the electrical connectors 342a configured as plugs of the shelves 342 or vice versa (e.g., USB-C receptacles and plugs).

The electrical connectors 331b of the shelving structure 131 may be coupled to the shelving structure 131 in a fixed manner (e.g., being rigidly coupled to the shelving structure 131) or movable manner (e.g., being flexibly or otherwise movably coupled to the shelving structure 131, such as on the end of a flexible cord that is coupled to the shelving structure 131). The electrical connectors 342a of the shelves 342 may be coupled to the shelves 342 in fixed manners (e.g., being rigidly coupled do the to the shelves 342) or movable manners (e.g., being flexibly or otherwise movably coupled to the shelves 342). In the case of the electrical connectors 342a being fixed to the shelves 342, either the mechanical coupling of the shelves 342 to the shelving structure 131 causes electrical coupling of the electrical connectors or the electrical connectors 331b of the shelving structure 131 are movable to be coupled to the electrical connectors 342a of the shelves 342.

The electrical connectors 331b may be provided in suitable numbers, positions, and configurations to accommodate different numbers of the shelves 342 in the different vertical shelf positions 331a on the shelving structure 131. In one example, the electrical connectors 331b, 342a are cooperatively sufficiently movable relative to the shelving structure 131 and the shelves 342, respectively, for one of the electrical connectors 331b and one of the second electrical connectors 342a of one of the shelves 342 to be connected when the one shelf 342 is at different ones of the vertical shelf positions 331a, such as shelf positions 331a that are spaced apart up to a distance (e.g., up to two feet, one and one half feet, or one foot or less) and/or a number of the vertical shelf positions 331a apart (e.g., up to ten, eight, five, four, three, or two of the vertical shelf positions 331a). For example, each one of the electrical connectors 331b may be provided in position and correspond to multiple of the vertical shelf positions 331a (e.g., fewer of the electrical connectors 331b than the predefined shelf positions 331a). In the case of the electrical connectors 331b being fixedly coupled and in fewer number than the vertical shelf positions 331a, the electrical connectors 342a of the shelves 342 are movably coupled thereto to reach from different ones of the vertical shelf positions 331a to one of the electrical connectors 331b of the shelving structure 131. In the case of the electrical connectors 331b of the shelving structure 131 being movably coupled and in fewer numbers than the pre-defined shelf locations, the electrical connectors 331b are sufficiently movable to reach the electrical connectors 342a (fixed or movable) of the shelves 342.

In another example, the electrical connectors 331b, 342a are cooperatively configured (e.g., insufficiently movable) for the electrical connectors 331b of the shelving structure 131 and the electrical connectors 342a of the shelves 342 to be connected when each of the shelves is at only one of the vertical shelf positions. That is, the electrical connector 342a of any given shelf 342 must be connected to a different one of the electrical connectors 331b of the shelving structure 131 if that shelf 342 is moved to a different vertical shelf position 331a. For example, one of the electrical connectors 331b may be provided in position and correspond to only one of the vertical shelf positions 331a (e.g., the same number of the electrical connectors 331b as the vertical shelf positions 331a).

Further referring to FIG. 4, each of the shelf locations 344 on the shelf 342 (e.g., the shelf 342-2 being used as an example) includes one or more of the weight sensors 134 and a shelf panel 332c that supports the container 346 of the medical supplies (e.g., a box or a bin) thereon. The one or more weight sensors 134 transfer force from the shelf panel 332c to the horizontal members 332b and thereby measure the weight therein, which may include the weights of the shelf panel 332c supported thereby, the container 346 positioned thereon, and the medical supplies contained therein. More preferably, for each of the shelf locations 344, the one or more weight sensors 134 are configured to transfer substantially all vertical force from the shelf panel 332c (e.g., including the container 346 thereon and the medical supplies therein) to the horizontal members 332b. In one example, the each shelf location 344 includes four of the weight sensors 134 that are positioned at front left, front right, rear left, and rear right positions to support corresponding corners of the shelf panel 332c (see, e.g., the left-most shelf in FIG. 4). In another example, the shelf location includes one of the weight sensors 134, which may be positioned centrally, such as between and supported by the horizontal members 332b and between left and right sides of the shelf location 344 and/or the shelf panel 332c (see e.g., the second shelf from the left in FIG. 4). Each of the different shelf locations 344 may have the same or different numbers of the weight sensors 134.

Figure 5:
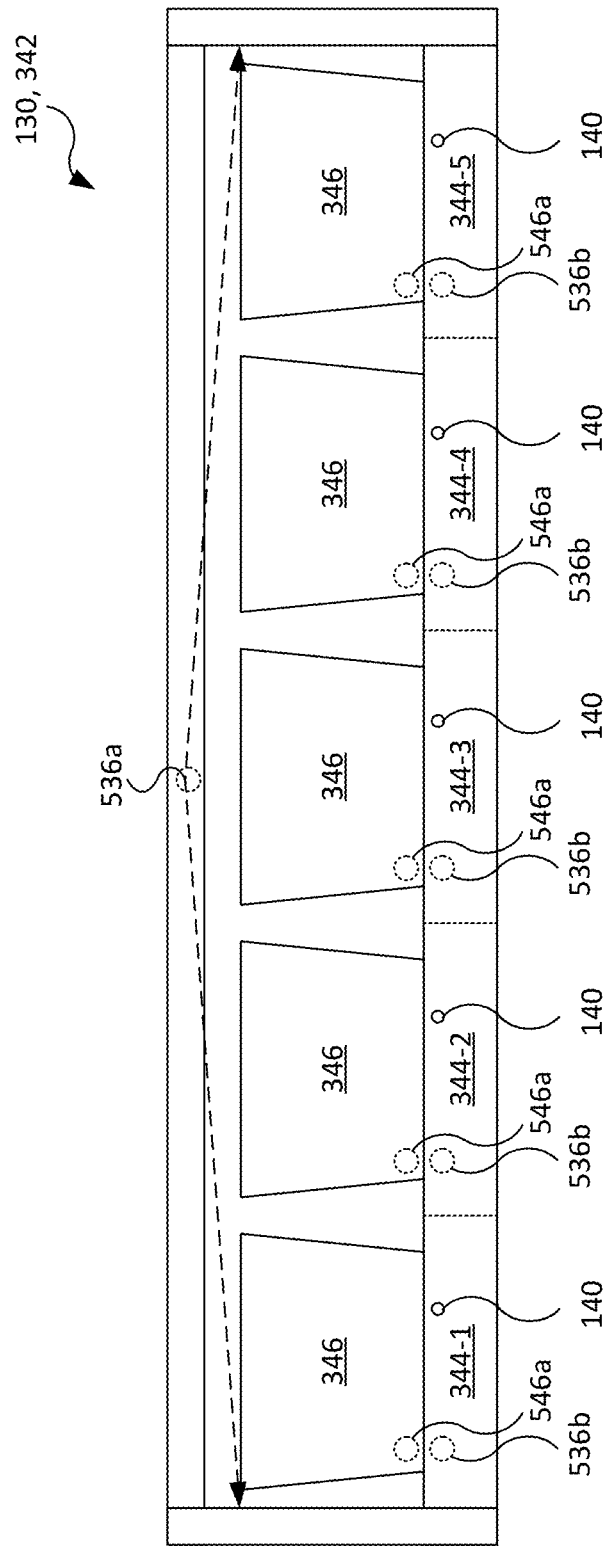
FIG. 5 is a front detail view of a shelf of the shelving unit.

Referring to FIG. 5, the shelving unit may further include the secondary sensors 136 and/or the indicators 140 as referenced previously. The secondary sensors 136 include activity sensors 536a and may further include container identification sensors 536b. The control system 132 (e.g., a primary controller 632c thereof) is in communication with the activity sensors 536a and/or the container identification sensors 536*b* to receive signals therefrom (e.g., activity signals and/or identifier signals) and may send further signals (e.g., causing the communications interface to send such signals) to the inventory computer system 110 according to signals received therefrom (e.g., including activity information, such as whether or not activity occurred, and/or identifying information, such as container identifiers).

Referring to FIG. 5, the activity sensors 536*a* are configured to detect physical activity that is indicative of (e.g., a proxy to) users removing the containers 346 and/or the medical supplies contained therein. As discussed in further detail below, such information may be used to corroborate weight changes and possible changes to the inventory of the medical supplies. In one example, the activity sensor 536*a* is configured to monitor activity associated with the entire shelving unit 130 or may instead be configured to primarily monitor activity associated with one of the shelves 342 of the shelving unit 130. In one specific example, the activity sensor 536*a* is a motion sensor, such as a passive infrared (PIR) sensor, that detects motion. The activity sensor 536*a* may, for example, be mounted to the horizontal member 332*b* above the shelf 342 monitored thereby and have a field of view (indicated by dashed lines) over the entire width of the shelf 342. In another example, the activity sensor 536*a* is a photoelectric sensor in (e.g., having a transmitter and a receiver that are spread apart or collocated in a retroreflective arrangement) that outputs a beam across the shelf 342 and sense interruption thereto. In still further examples, the activity sensors 536*a* may include cameras and associated machine-vision software that may detect and/or identify motion, people, and/or objects.

Still referring to FIG. 5, the container identification sensors 536*b* may be configured to identify the container 346 in a given shelf location 344. The container identification sensor 536*b* may, for example, be configured to read a container identification tag 546*a* that each (or some) of the containers 346 includes. The container identification sensors 536*b* read the container identification tags 546*a* to identify the containers 346 to distinguish therebetween. For example, each of the container identification tags 546*a* may include a unique identifier (e.g., a container identifier) that is associated by the inventory computing system 110 with the container 346 (e.g., in a database) and a particular medical supply to be contained therein. In one example, each of the shelf locations 344 includes one of the container identification sensors 536*b*, which is a radio frequency identification (RFID) sensor, and the container identification tag 546*a* is an RFID tag. The container identification sensor 536*b* may also be considered to be an activity sensor by detecting the container identification tags 546*a* and, thereby, placement and removal of containers 346 having the container identification tags 546*a*.

The container identification sensors 536*b* and the container identification tags 546*a* are positioned on the shelf locations 344 and the containers 346, respectively, to facilitate reading of the container identification tag 546*a* of the container 346 positioned thereon and to avoid reading of the container identification tag 546*a* of the container 346 positioned on a shelf location 344 adjacent thereto. For example, the container identification sensors 536*b* may be positioned proximate a forward edge of the shelf panel 332*c*, and the container identification tag 546*a* may be positioned proximate a forward edge of the container 346 on a lower portion thereof (e.g., inside the container).

Still referring to FIG. 5, the shelving unit 130 may include one or more of the indicators 140, which are configured to communicate information about the shelving unit 130, the shelves 342, the shelf locations 344, and/or the medical supplies. The one or more indicators 140 may, for example, include light emitting diodes (LED) that are illuminated to indicate information. For example, the indicators 140 may be illuminated different colors and/or flash in different patters to indicate different information. The different information indicated by the indicators 140 may, for example, include inventory health (e.g., amount of medical supplies relative threshold amounts, as discussed in further detail below), inventory errors (e.g., misplacement of medical supplies and/or the containers 346), and/or equipment status (e.g., if operational, in a restocking state, or if error conditions are present).

In one example, the shelving unit 130 includes one of the indicators 140 positioned in association with each one of the shelf locations 344 (e.g., positioned on or below the shelf panel 332*c*, such as on the horizontal member 332*b*). The indicators 140 are illuminated in manners corresponding to indications displayed by the user interface device 120, as discussed in further detail below. For example, the indicator 140 may illuminate different colors to indicate different inventory healthy, for example, whether the quantity of the medical supplies stored at that shelf location 344 requires action (e.g., green if adequate, yellow if restocking is needed soon, or red if restocking is required immediately).

In another example, the shelving unit 130 instead or additionally includes one of the indicators 140 that indicates information about the shelving unit 130 as a whole (e.g., whether one or more of the shelf locations 342 or the containers 346 requires restocking or is empty).

Figure 6:
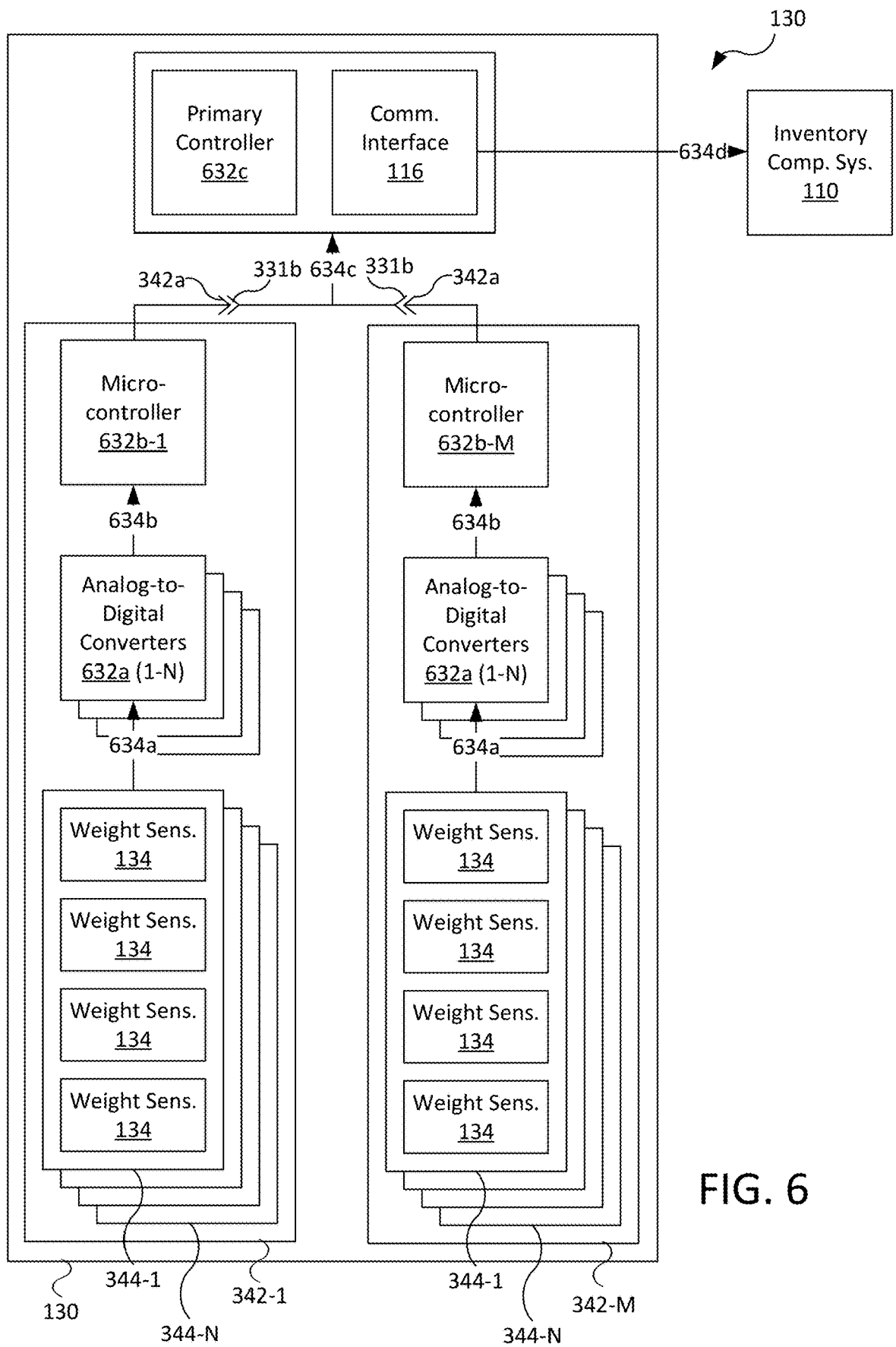
FIG. 6 is a schematic view of the inventory system illustrating a control system of the shelving unit.

Referring to FIG. 6, each shelf location 344 on each shelf 342 of the shelving unit 130 is configured to measure the weight thereon, which functions as a proxy to the quantity of medical supplies stored thereon. As discussed in further detail below, the inventory computing system 110 receives the weight measurements of each of the shelf locations 344 and deducts weights of non-medical supplies thereon (e.g., of the shelf panels 332*c* and the containers 346) to determine the weight of the medical supplies.

The control system 132 is configured to operate the weight sensors 134, receive measurement signals therefrom, and send weight information to the inventory computing system 110. For example, the control system 132 is in communication with the weight sensors 134 to receive measurement signals from the weight sensors 134, determine weight measurements according to the measurement signals for each of the shelf locations 344, and then send the weight measurements to the inventory computing system 110 via the network. The inventory computing system 110 may then determine the weight measurements for the shelf locations (e.g., of the medical supplies thereon) and then calculates quantities of the medical supplies stored.

Each of the weight sensors 134 is configured to measure vertical force (i.e., weight) applied thereto and outputs a first signal 634*a* that indicates the force measured thereby (e.g., a weight value) or a proxy thereto (e.g., a voltage). Each of the weight sensors 134 may, for example, be a strain gauge or a load cell that outputs the first signal 634*a* as a voltage. As mentioned previously, each shelf location 344 may include any suitable number of the weight sensors 134 (e.g., four of the weight sensors 134 with one at each of four corners of the shelf location 344 and/or the shelf panel 332*c*, or one of the weight sensors 134 at a central position of the shelf location 344 and/or the shelf panel 332*c*).

The control system 132 is configured to receive and process the first signal 634*a* to determine a weight measurement. The control system 132 includes one or more analogto-digital converters 632a (ADC), one or more shelf microcontrollers 632b, and a primary controller 632c. The ADC 632a converts the first signal 634a from the voltage to a numerical value output by the ADC 632a in a second signal 634b. The shelf microcontroller 632b converts the numerical value from the second signal 634b to a weight measurement output by the shelf microcontroller 632b in a third signal 634c. The primary controller 632c receives the third signal 634c and consolidates and sends a fourth signal 634d with the weight measurements (e.g., for each of the shelf locations 344) to the inventory computing system 110 via the communications interface 116 (e.g., in a table or database that may include the container identifier if so equipped). The primary controller 632c may, for example, be configured as described for the controller 114.

In the non-limiting example configuration shown in FIG. 6, multiple of the weight sensors 134 output the first signal 634a to a common ADC 632a (e.g., one of the ADC's 632a receives the first signal 634a from four of the weight sensors 134 of one shelf location 344), multiple of the ADC's output the second signal 634b to a common microcontroller 632b (e.g., one of the microcontrollers 632b receives the second signal 634b from all the ADC's 632a corresponding to one of the shelves 342), and multiple of the microcontrollers 632b output the third signal 634c to the primary controller 632c (e.g., one primary controller is provided for each of the shelving units 130).

The shelving unit 130 may be configured to measure the weight of each shelf location 344 at suitable intervals (e.g., every sixty seconds), upon certain events (e.g., upon detecting user activity), and/or when otherwise requested (e.g., by the inventory computing system 110, such as when first associating the shelf locations 344 with different medical supplies and/or upon restocking). In some configurations, the shelving unit 130 may store weight measurements at different times and send weight measurements from before and after detected activity. The weight measurements from before detected activity may be compared to weight measurements previously stored by the inventory computing system 110 to detect and/or account for sensor drift. The shelving unit 130 may send the weight measurements in batches, for example, including the weight measurements for all shelf locations 344 of the shelving unit (e.g., in a database associating the shelf location 344 and/or the container identifier with the weight measurement). The shelving unit 130 may further send information from the activity sensor 536a in conjunction with the weight measurements, which may be used by the inventory computing system 110.

The inventory computing system 110 is configured to determine the current estimated quantities of medical supplies stored by one or more of the shelving units 130 according to the weight measurements. More particularly, the measured weight of each shelf location 344 may be used as a proxy to estimate the quantity of the medical supply. Starting with a known quantity of the medical supply, a current quantity of the medical supply (e.g., at each shelf location) may be estimated (e.g., determined) from changes in the measured weight and a known incremental weight of the medical supply (e.g., an incremental weight). Alternatively, the quantities of the medical supplies may be determined directly according to the weight measurements and the incremental weights of the medical supplies, without starting with a current quantity of the medical supply, while accounting for other sources of weight in the weight measurement (e.g., of the shelf panel and/or container thereon).

Furthermore, the inventory computing system may perform other functions, for example, identifying potential errors in current quantity estimations, providing indicators of quantity levels, estimating total quantities of medical supplies (e.g., stored by the shelving units 130 in combination with other storage), determining usage trends and order medical supplies, and/or identifying aberrant usage (e.g., relative to trends).

As referenced above, a current quantity estimation may be derived from changes in weight measurements and an incremental weight for the medical supply.

To determine the incremental weight of the medical supply, the inventory computing system 110 first determines a zeroed weight measurement the shelf location 344, which is the weight measured by the weight sensors 134 with shelf panel 332c and/or the container 346 thereon but no medical supplies. Upon placement of a known quantity of the medical supply associated with the shelf location 344 and input of that quantity to the inventory computing system 110 (e.g., with the user interface device 120), the inventory computing system 110 determines an incremental weight of that medical supply. For example, for a given medical supply, the incremental weight may be calculated as follows:

$$W\_incremental = (W\_measured - W\_zeroed)/Q\_initial \quad (1)$$

where W_incremental is the incremental weight of the medical supply, W_measured is the weight measurement for the shelf location 344, W_zeroed is the zeroed weight measurement for the shelf location 344, and Q_initial is the known initial quantity of the increment of the medical supply.

Depending on the weight and/or packaging of the medical supply, the increment of the medical supply may be a singular unit, a package, or a quantity in which cases the incremental weight may be a per unit weight, a per package weight, or a per quantity weight, respectively. For example, for heavier supplies, the incremental weight is a per unit weight of that medical supply (e.g., weight for each stent). For bulk packaged supplies, the incremental weight may be a per package weight of that medical supply (e.g., a package of disposable gloves). For relatively light supplies, the incremental weight may be a per quantity weight of that medical supply (e.g., weight per 20 disposable gloves).

A current quantity of the medical supply is incremented upward or downward as the medical supply is added to or removed from the container 346, respectively, according to changes in the measured weight and the incremental weight of the medical supply. For example, starting with the current quantity equaling the known quantity (e.g., when the incremental weight is first determined), the current quantity is incremented downward. Furthermore, the current quantity may updated as known quantities of the medical supply are added to or removed from the shelf location 344 (e.g., when the shelf location 344 is restocked at or redistributed from the shelf location 344) and such known quantity is input to the inventory computing system 110 (e.g., with the user interface device 120). For example, the current quantity of a medical supply may be calculated as follows:

$$Q\_current = Q\_initial + (\Delta W\_measured/W\_incremental) + Q\_change \quad (2.1)$$

where Q_current is the current quantity of the increment of the medical supply estimated according to the weight measurements, Q_initial is previous known or calculated quantity of the increment of the medical supply, ΔW_measured is the change in the measured weight of the shelf location 344, W_incremental is the incremental weight of the medical supply, and Q_change is the known quantity of the increment of the medical supply added to or removed from the shelf location 344. In equation 2.1, it should be noted that Q_current would be updated according to either ΔW_measured or Q_Change at a given time, but not both so as to not double count added supplies based both on the change in the measured weight and the known quantity added or removed.

The current quantity may instead or additionally be calculated directly from the weight measurements without calculating a change in quantity and/or without reference to a previous quantity. For example, the current quantity of the medical supply may be calculated as follows:

$$Q\_current = W\_measured/W\_incremental \qquad (2.2)$$

Furthermore, the current quantity may be reset to a known quantity input to the inventory computing system 110 (e.g., with the user interface device 120), for example, when restocking with a known quantity of the medical supplies and a manual recount is performed by the person performing the restocking. In such case, the current quantity is equal to the known quantity, as follows:

$$Q\_current = Q\_verified \qquad (3)$$

where Q_verified is the known quantity of the increment of the medical supply as counted or otherwise known and input by the user. Input of known quantities of the medical supply with the user interface device 120 is discussed below. Q_verified may be substituted for Q_initial in equation (1) above.

The current quantity and other values described in the equations (1), (2), and (3) may be stored in the database. The weight measurements may be further processed to account for sensor drift over time and/or to de-noise the weight measurements therefrom according to any suitable methods, for example, by use of a Kalman filter.

Furthermore, data from the activity sensors 536a and/or the container identification sensors 536b may be stored in the database and/or utilized when calculating the current quantities for each of the shelf locations 344. For example, if no activity is detected corresponding in time to changes in weight measurements, such changes in weight measurements may instead indicate an error in the weight sensors 134, such as sensor drift or a fault therein. Instead or additionally, the activity information and the weight measurements may be processed cooperatively, such as with a Kalman filter, for example, with the activity information (e.g., binary information of whether activity has been detected or not, such as motion or placement or removal of a container 346 having a container identification tag 546a) being a strong indicator of whether or not changes in weight measurements correspond to changes in quantities of the medical supplies.

Personnel activity may still further be used to identify changed quantities the medical supplies and/or to track usage of the medical supplies. Personnel may, for example, provide an electronic key to a security or access control system of the facility to access a location in which the shelving units 130 are positioned (e.g., a storage room), and the access data (e.g., time of access and/or personnel) may be used to further corroborate changes in quantities in conjunction with the weight measurements (e.g., with a Kalman filter) and/or track changed quantities to particular personnel. Instead or additionally, one of the secondary sensors 136 of the shelving unit 130 may be configured to receive the electronic key, for example, using RFID.

As referenced above, in addition to estimating the current quantity of the medical supplies, the inventory computing system 110 may perform other functions based on the weight measurements at each shelf location 344 and/or the estimates of current quantity derived therefrom.

The inventory system 100 may be configured to visually indicate whether action is appropriate regarding the inventory of medical supplies in the shelf locations 344, each shelving unit 130 overall, and/or an overall inventory (e.g., multiple shelving units 130 and/or other storage). Whether action is appropriate regarding the inventory of the medical supplies may also be referred to as inventory health.

Whether action is appropriate (e.g., the inventory health) may be determined according to the current quantity of the medical supplies relative to one or more inventory standards that may, for example, be based on the estimated quantity at the shelf location 344 or an overall inventory of the medical supply (e.g., at other shelf locations 344 on other shelving units 130 and/or other storage). The inventory standards may, for example, be a fixed quantity (e.g., a number), a relative quantity (e.g., percentage of a maximum storage quantity or of packaged quantities), a projected usage (e.g., time horizon for using entire stock of the medical supply of a shelf location 344), or a combination thereof (e.g., quantity or relative quantity projected to remain at a time horizon). The inventory standard may be manually determined and input or be determined by the inventory computing system 110.

An assessment of whether action is appropriate (e.g., the inventory health) is determined by the inventory computing system 110, while the corresponding indicator (e.g., an inventory health indicator) is output by the shelving units 130 (e.g., the indicators 140 thereof) and/or by the user interface device 120 (e.g., a visual interface thereof). The inventory computing system 110 sends signals to the shelving units 130 and/or the user interface device 120 to output the inventory health indicator.

In one example, the inventory health indicators may be color-coded, such as a green indicating no action is required (e.g., good health), yellow indicating some action will be required in the near term (e.g., restocking the shelf location 344 and/or re-ordering the medical supply), and/or red indicating that action is presently required. In the case of the shelving unit 130 providing the inventory health indicator, the indicator 140 may be illuminated a color corresponding to the inventory health. In the case of the user interface device 120 providing the inventory health indicator, a graphical representation may represent the shelving unit 130 and/or the shelf locations 344 thereon, while the inventory health indicator is displayed in spatial association with the shelf locations 344 (e.g., the graphical representation of the shelf location 344 colored or shaded with the color corresponding to the inventory health). If both the shelving unit 130 and the user interface device 120 are configured to display the health indicator, they both may output the same color as the inventory health indicator provided thereof. In the case of the health indicator being provided for the shelving unit 130 as a whole, the inventory health indicator may be output according to the most imminent action required of any shelf location 344 thereof (e.g., whether action is currently required for any one of the shelf locations 344 or the medical supply associated therewith).

The user interface device 120, including the graphical representations for the health indicators, is discussed in further detail below.

The inventory system 100 may be configured to detect possible misplacement of medical supplies in different ones of the containers 346 and/or misplacement of the containers 346 at incorrect shelf locations 344 according to the weight measurements.

The inventory computing system 110 may identify possible misplacement of the medical supplies if the changes in weight measurement received for a shelf location 344 do not correspond to the weight increment for the medical supply associated with that shelf location 344. For example, if the expected medical supply has an incremental weight of 32 ounces and the inventory computing system 110 receives a weight measurement changes by 16 ounces, the inventory computing system 110 may identify a possible misplacement of the medical supplies. Upon detection of possible misplacement the medical supplies, the inventory computing system 110 may, accordingly, output one or more signals according to which a misplacement indicator may be output by the shelving unit 130 (e.g., with the indicator 140 of the shelf location 344, for example, blinking or changing color, and/or the graphical representation provided by the user interface device 120 providing an indication).

The inventory computing system 110 may identify possible misplacement of the container 346 according to the weight measurements. For example, if two of the containers 346 are each removed from the shelf locations 344 associated with the medical supply contained therein and replaced at the shelf location 344 of the other of the two containers 346, the weight measurements may be used to identify such misplacement (e.g., if the weight measurements at each of the two shelf locations 344 prior to removal correspond to the weight measurements at the other of the two shelf locations 344 after replacement, for example, based on the weight measurement itself and/or a quantity of the medical supply determined thereby). Upon detection of possible misplacement of the containers 346, the inventory computing system 110 may, accordingly, output one or more signals according to which a misplacement indicator may be output by the shelving unit 130 (e.g., with the indicators 140 of the shelf locations 344, for example, blinking or changing color, and/or the graphical representation provided by the user interface device 120 providing such indication).

In embodiments in which the shelving unit 130 includes the container identification sensor 536b and the containers 346 include the container identification tags 546a, when one of the containers 346 is misplaced at a different shelf location 344, the container identification sensor 536b at the new shelf location 344 identifies the container 346 misplaced thereon, and the control system 132 sends a signal to the inventory computing system 110 which may then re-associate that container 346 (e.g., the container identifier) and/or the medical supplies contained therein to the new shelf location 344 or an indication or other notification may be provided to the user.

The inventory system 100 may be configured to determine overall quantities of the different medical supplies of multiple different shelving units 130 and/or other inventory. For example, a particular medical supply may be both kept on multiple different shelving units 130 (e.g., medical supply closets associated with different operating rooms, floors of a hospital, or different buildings within a medical campus) and other inventory (e.g., other storage areas). The inventory computing system 110 may determine overall quantities of the particular goods with the current quantities determined for each of the shelving units 130 (as described previously), while receiving inventory information (e.g., quantities) from other sources (e.g., another ordering and/or inventory system in which the medical supplies or packages thereof are more directly tracked, such as with scanning such supplies or packages upon receipt and/or removal).

The inventory system 100 and, in particular, the inventory computing system 110 may be configured to determine trends in the inventory of medical supplies, for example, with particular shelving units 130 and/or a group of shelving units 130. Such trends may, for example, include baseline usage over a period of time (e.g., day, week, month, or year), changes in usage over time (e.g., increasing or decreasing), peak usage times, and/or aberrant usage (e.g., significant changes from baseline) for one of the shelving units 130, a group of the shelving units 130, or all shelving units 130. The baseline usages and changes in usage may be used, for example, for automated ordering of the medical supply (e.g., to maintain minimum quantities based on current quantity, expected usage, and lead time), as well as to determine the inventory health (i.e., as described previously). In the case of aberrant usage, the inventory computing system 110 may be configured to provide a notification, for example, with the user interface device 120 or another message (e.g., an email message).

The user interface device 120 is configured for a user to configure and reconfigure the inventory system 100, input known quantities of the medical supplies (e.g., when restocking), and provide various indicators and notifications (e.g., the inventory health notifications, described previously).

The inventory system 100 is configured to associate medical supplies with the shelf locations 344. Unique medical supplies may be associated (e.g., assigned) to one or more of the shelf locations 344, while each shelf location 344 may be associated with only one unique medical supply. For example, each medical supply may have a unique identifier, which may be referred to as a supply identifier, such as a stock-keeping unit (SKU) or assigned number. Each shelf location 344 may have a unique identifier (e.g., an assigned number) or a series of identifiers that uniquely identify the shelf location 344 from others of the shelf locations 344 (e.g., an assigned identifier for the shelving unit 130 thereof and the position thereon, such as a number and lateral position number), which may be referred to as a location identifier. The medical supply is associated with the shelf location 344, for example, by being stored in association with each other in a database by the inventory computing system 110. The incremental weight, current quantity, and other values described above with respect to the equations (1), (2), and (3) may also be stored in the database by the inventory computing system 110. For example, a first database may store the supply identifiers in association with the incremental weights for such supplies, while a second database may store the location identifiers in association with the supply identifiers of the supplies there stored, along with the current weight (i.e., measured at the shelf location) and/or current quantity of the supplies derived from the current weight and incremental weight. Any other suitable database structures may be utilized by which the supply, supply identifier, incremental weight, shelf location, current weight, and current quantities are stored for association with each other.

A given medical supply may be associated with more than one shelf location 344 on a given shelving unit 130 (e.g., occupying adjacent shelf locations 344 for larger medical supplies or larger container 346 occupying the combined width of two adjacent shelf locations 344, as was described for the two left-most shelf locations 344-1, 344-2 on the shelf 342-3) or different shelving units 130 (e.g., on different floors of a hospital). For example, the inventory system 100 is configurable to associate, with the inventory computing system 110, any one of the shelf locations 344 with a first of the medical supplies and any two, three, or more adjacent ones of the shelf locations 344 with a second of the medical supplies. The inventory computing system 110 may then determine the quantity of the first medical supply with the weight measurements for the first shelf location (e.g., according to any of the formulae and methods described previously), and may further determine the quantity of the second medical supply with the weight measurements for the other two adjacent shelf locations 344 (e.g., combining the weight measurements and using the formulae and methods described previously). In this manner multiple ones of the shelf locations 344 may each be associated with only one medical supply to determine the quantity thereof, while multiple sets of adjacent shelf locations 344 may each be associated with only one medical supply to determine the quantity thereof. While one medical supply may be associated with more than one of the shelf locations 344, each shelf location may be associated with only one of the medical supplies at a given time.

The user interface device 120 receives inputs according to which the medical supplies are associated with the different shelf locations 344, which are sent to the inventory computing system 110. For example, the user interface device 120 may output a graphical representation of the shelving unit 130 from which the user may select one of the shelf locations 344 and input the supply identifier (e.g., manually or by scanning a quick response (QR) code from packaging of the medical supply).

The inventory system 100 is configured to receive inputs of known quantities of medical supplies that are being placed at the shelf location 344. For example, when initially stocking or restocking a shelf location 344 of the medical supply, the user may input a known quantity of the medical supply. For example, the user interface device 120 may output a graphical representation of the shelving unit 130 from which the user may select one of the shelf locations 344 and input the known quantity. The user interface device 120 may prompt or otherwise allow the user to select whether the known quantity of the medical supply that is being added to the existing inventory of the shelf location 344 (e.g., Q_change, as described above) or the total quantity of the medical supply at the shelf location counted or otherwise verified by the user (e.g., Q_initial or Q_verified, as described above). The user interface device 120 sends such known quantities of the medical supply to the inventory computing system 110. Alternatively, the inventory system 100 may determine the added or removed quantity of a supply at a shelf location 344 from the weight measurement without further input by the user (e.g., of a specific quantity being added or removed).

The inventory system 100, as described previously, may be configured to provide inventory health indicators with the user interface device 120. For example, referring to FIGS. 7 and 8, and as referenced previously, the user interface device 120 may be configured to output graphical representations of multiple of the shelving units 130 (as shown in FIG. 7) and of individual ones of the shelving units 130.

Figure 7:
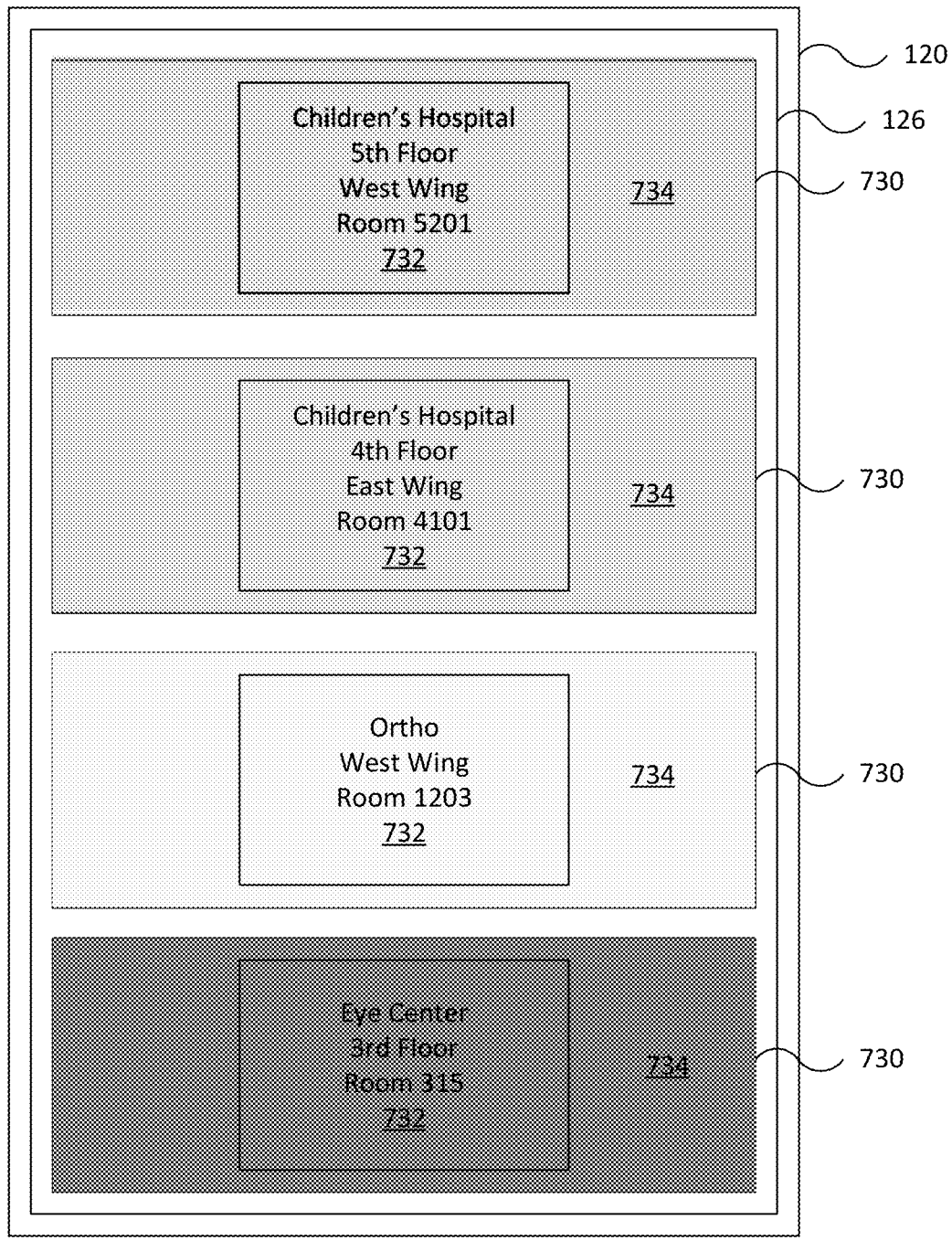
FIG. 7 is a graphical representation of multiple shelving units with inventory health indicators output by a user interface device of the inventory system.

As shown in FIG. 7, the user interface device 120 is configured to display graphical representations 730 of multiple ones of the shelving units 130. For example, the graphical representations 730 may be of the shelving units 130 on different floors of a hospital, different storage rooms on a floor of a medical building, or different shelving units 130 within a single storage room. Each of the graphical representations 730 may include a shelf description 732 that describes the shelving unit 130 corresponding thereto, for example, including a description of the location (e.g., building, floor, wing, and/or room number). The graphical representations 730 may further include health indicators 734 (e.g., represented by different colors and/or shading in the drawings), which may be provided in the form of a color or shading. The shelf description 732 and the health indicators 734 may be provided according to information stored and received from the inventory computing system 110.

Each graphical representation 730 of one of the shelving units 130 may be selectable, for example, subsequently showing a graphical representation of that individual shelving unit 130 (e.g., received from the inventory computing system 110) or to input information thereabout.

Figure 8:
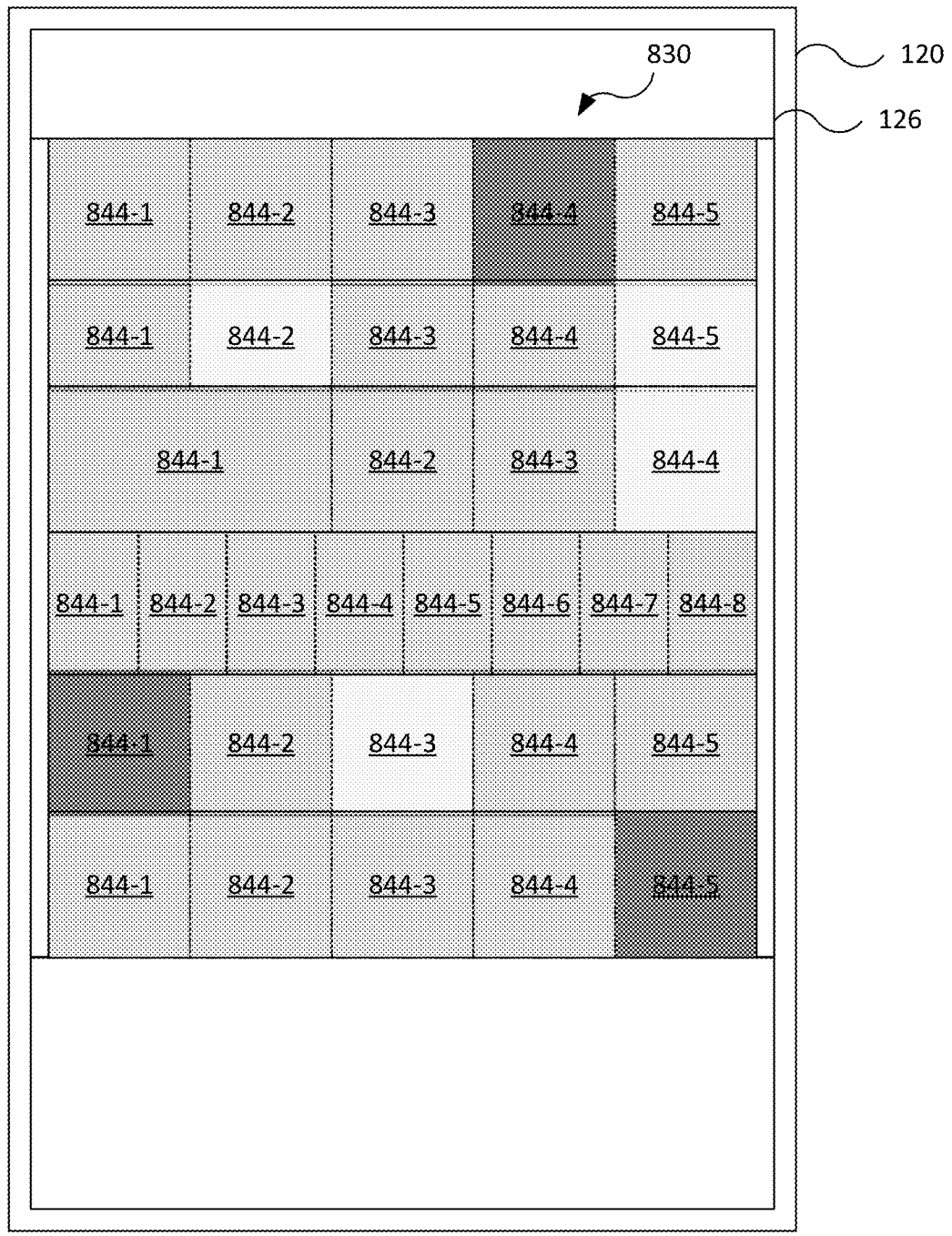
FIG. 8 is a graphical representation of a shelving unit with inventory health indicators output by the user interface device.

As shown in FIG. 8, the user interface device 120 is configured to display graphical representations 830 of individual shelving units 130, which includes graphical representations 844 of the shelf locations 344 thereof. For example, the graphical representation 830 represents the shelving unit 130 illustrated in FIG. 3. The graphical representation 830 may further include inventory health indicators (not labeled) for each of the shelf locations 344 (e.g., shown as different colors or darkness of shading). The graphical representation 830 may still further include information about the shelf locations 344, such as an indicator, description, and/or quantity of the medical supplies stored thereon (not shown) as determined by and received from the inventory computing system 110.

Each graphical representation 844 of one of the shelf locations 344 may be selectable, for example, subsequently displaying more information about the medical supplies (e.g., usage trends), misplacement errors (described previously), and/or to input information thereabout (e.g., to associate a different medical supply with the shelf location and/or to input a known quantity (e.g., Q_initial, Q_change, or Q_verified), such as when setting up or restocking the shelf location 344.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An inventory system comprising:
one or more shelving units that each includes shelves for storing medical supplies, a control system, and a communications interface, wherein:
each of the shelves includes shelf locations that are discrete locations spread laterally thereacross at which weight supported by the shelf is measured with weight sensors independent of all others of the shelf locations of that same shelf, and each of the shelf locations includes one or more of the weight sensors for measuring the weight supported thereat,
the control system is in communication with the one or more weight sensors for receiving measurement signals therefrom and causing the communications interface to send weight measurements for each of the shelf locations of each of the shelves determined according to the measurement signals, and
each of the one or more shelving units further includes an activity sensor configured to detect activity associated with one or more of the shelf locations, and the control system is in communication with the activity sensor for receiving activity signals therefrom and causing the communications interface to send activity information according to the activity signals; and an inventory computing system in communication with each of the one or more shelving units via a network to receive the weight measurements for the shelf locations and the activity signals, wherein the inventory computing system associates each of the shelf locations with only one of the medical supplies at a time, and determines a quantity of each of the medical supplies stored on each of the shelf locations according to the one or more weight measurements for the shelf location associated therewith and the activity information.

2. The inventory system according to claim 1, wherein the inventory system is configurable to associate, with the inventory computing system, any one of the shelf locations with a first of the medical supplies and any two adjacent ones of the shelf locations with a second of the medical supplies, and wherein the inventory computing system determines a first quantity of the first medical supply according to the weight measurements for the one shelf location, and determines a second quantity of the second medical supply according to the weight measurements for the two adjacent shelf locations;

wherein each of the shelving units includes a shelving structure that is cooperatively configured with the shelves for the shelves to be moved between different vertical shelf positions and to electrically couple the weight sensors of the shelves to a controller of the control system at each of the vertical shelf positions; and wherein each of the shelving units is configured to communicate with the inventory computing system predominantly cellularly independent of the other network and secondarily with the other network.

3. The inventory system according to claim 1, wherein for each shelf location, the inventory computing system determines the quantity of the medical supply stored thereon according to the one or more weight measurements received for the shelf location and an incremental weight of the medical supply stored thereon.

4. The inventory system according to claim 3, wherein the inventory computing system determines the incremental weight for at least one of the medical supplies according to the weight measurement of a known quantity of the at least one medical supply on the shelf location, a zeroed weight measurement when none of the medical supplies are on the shelf location, and the known quantity of the at least one medical supply.

5. The inventory system according to claim 1, wherein the inventory computing system associates any one of the shelf locations with a first of the medical supplies and any two adjacent ones of the shelf locations with a second of the medical supplies; and wherein the inventory computing system determines a first quantity of the first medical supply according to the weight measurements for the one shelf location, and determines a second quantity of the second medical supply according to the weight measurements for the two adjacent shelf locations.

6. The inventory system according to claim 1, wherein each of the shelving units includes a shelving structure that is cooperatively configured with the shelves for the shelves to be moved between different vertical shelf positions and to electrically couple the weight sensors of the shelves to a controller of the control system at each of the vertical shelf positions.

7. The inventory system according to claim 6, wherein each of the shelving units includes a first electrical connector and each of the shelves includes a second electrical connector that is releasably connectable to the first electrical connector to electrically couple the weight sensors to the controller; and wherein the first electrical connector and the second electrical connector are together sufficiently movable relative to the shelving structure and the shelf, respectively, for the first electrical connector and the second electrical connector to be connected when the shelf is at different ones of the vertical shelf positions.

8. The inventory system according to claim 6, wherein each of the shelving units includes first electrical connectors associated with each of the vertical shelf positions and the shelves include second electrical connectors that releasably connectable to the first electrical connectors to electrically couple the weight sensors to the controller; and wherein the first electrical connectors and the second electrical connectors are configured such that the second electrical connectors must be connected to a different one of the first electrical connectors when the shelves are moved to different ones of the vertical shelf positions.

9. The inventory system according to claim 1, wherein each of the shelving units is configured to communicate with the inventory computing system via the network cellularly independent of another network of a facility in which the shelving unit is located.

10. The inventory system according to claim 9, wherein each of the shelving units is configured to communicate with the inventory computing system predominantly cellularly independent of the other network and secondarily with the other network.

11. The inventory system according to claim 1, wherein the activity sensor is configured to detect activity associated with more than one of the shelf locations.

12. The inventory system according to claim 11, wherein each of the activity sensors is a motion sensor configured to detect motion proximate the shelf locations of at least one shelf, and wherein the activity is the motion.

13. The inventory system according to claim 1, wherein at least one of the shelves includes at least five shelf locations.

14. A shelving system comprising:
a shelving unit having:
shelves with shelf locations thereon, the shelf locations being spread laterally across each of the shelves and being discrete from each other;
weight sensors that are each associated with one of the shelf locations for measuring weight of supplies positioned on the shelf location associated therewith; and
one or more activity sensors for detecting physical activity associated with the shelf locations;
containers configured to hold medical supplies and that each include a container identification tag having a unique identifier; and
a control system that receives signals from the weight sensors and the one or more activity sensors and outputs to an inventory computing system weight measurements according to the weight sensors and activity information according to the one or more activity sensors;
wherein the control system associates the unique identifier of each of the containers with one of the medical supplies to be stored in the container having the container identification tag;

wherein the one or more activity sensors include container identification sensors that are each associated with one of the shelf locations and configured to read the container identification tags of the containers to identify the one of the containers on the shelf location associated therewith, and wherein the physical activity includes one or both of placement or removal of the container from the shelf location; and wherein when one of the containers is moved from one of the shelf locations to another of the shelf locations, the container identification sensor of the other shelf locations reads the container identification sensor of the one container and sends a signal to the control system according to which the control system one or more of associates the one container with the other shelf location, associates the medical supply stored in the one container with the other shelf location, or provides a notification to a user.

15. The shelving system according to claim 14, wherein the one or more activity sensors includes a motion sensor configured to detect motion proximate the shelf locations, and wherein the physical activity is the motion.

16. The shelving system according to claim 14, further comprising one or more visual indicators coupled thereto that indicate statuses of quantities of the supplies on the shelf locations.

17. The shelving system according to claim 14, wherein the control system is configured to send the weight measurements and the activity information in batches at predetermined intervals.

18. The shelving system according to claim 14, the container identifier of each container is associated with a shelf location at which the container is stored and a supply identifier of the one of the medical supplies stored in the container, only one of the medical supplies being associated with each of the container identifiers.

19. The shelving system according to claim 14, wherein each of the shelf locations is configured to receive only one of the containers thereon at a time.

20. A method for determining quantities of medical supplies comprising:
   providing a shelving unit having one or more shelves storing medical supplies, each of the one or more shelves including shelf locations that are discrete locations spread laterally thereacross at which weight supported by the shelf is measurable with weight sensors independent of all others of the shelf locations of that same shelf, and each of the shelf locations including one or more weight sensors for measuring the weight of one of the medical supplies supported thereat;
   storing, with a computing system, for each medical supply, a supply identifier and an incremental weight;
   storing, with the computing system, for each shelf location, the supply identifier of the medical supply stored therein and one or both of the weight measured by the one or more weight sensors or a quantity of the medical supply stored thereon;
   associating each of the shelf locations with only one of the medical supplies at a time;
   measuring, with one or more weight sensors, the weights of the medical supplies stored on the shelf locations;
   sensing physical activity associated with the shelving unit; and
   determining, with the computing system, the quantity of each of the medical supplies at each of the shelf locations according to the incremental weight of the medical supply, the weight measured at the shelf location, and the physical activity detected at the shelf location.

* * * * *